United States Patent [19]

Garton, Jr. et al.

[11] Patent Number: 4,536,154
[45] Date of Patent: Aug. 20, 1985

[54] EDGEWISE BRACKET

[75] Inventors: Robert E. Garton, Jr., Elkhart Lake; John E. Viglietti, Sheboygan, both of Wis.

[73] Assignee: American Orthodontics Corporation, Sheboygan, Wis.

[21] Appl. No.: 619,336

[22] Filed: Jun. 11, 1984

[51] Int. Cl.³ .............................................. A61C 7/00
[52] U.S. Cl. .......................................... 433/8; 433/16
[58] Field of Search ................................ 433/8, 16, 9

[56] References Cited
U.S. PATENT DOCUMENTS
4,415,330 11/1983 Daisley et al. ..................... 433/16

Primary Examiner—Robert Peshock
Attorney, Agent, or Firm—Lloyd L. Zickert

[57] ABSTRACT

An orthodontic bracket for use with an archwire to orthodontically treat a patient by imparting corrective forces to a tooth. The bracket includes a base portion for attachment to the tooth, mesial and distal tie wings extending from the base portion, each of which includes gingival and occlusal tips defining therebetween a buccolabial opening archwire slot. The archwire slots are in mutual alignment and define a reference line for orienting the bracket in parallel relation to the occlusal plane and the tie wings are oriented such that they are obliquely angled to the reference line. The gingival tips have surfaces that are in parallel alignment with the reference line and substantially equidistant therefrom, and the outer borders of the tie wings form a trapezoidal configuration as the tie wings are of unequal size.

8 Claims, 7 Drawing Figures

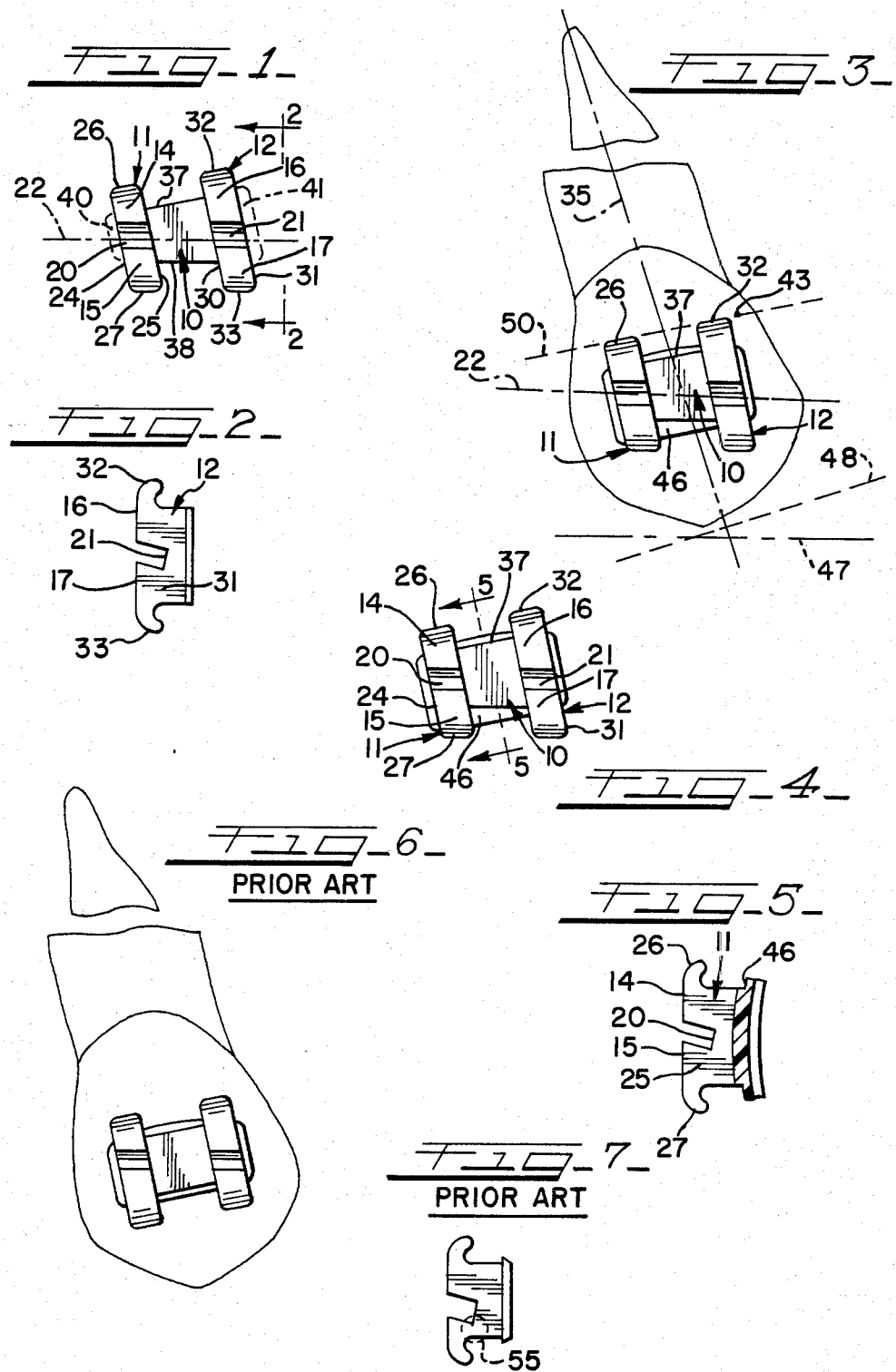

EDGEWISE BRACKET

DESCRIPTION

This invention relates in general to an orthodontic bracket for use in straightening teeth, and more particulary to an improved orthodontic bracket that includes reference points to facilitate mounting in proper alignment on a tooth and to provide torquing and/or tipping action which requires angulation of the archwire slots, and still more particularly to an improved bracket assembly that provides an easy-to-mount unit and which is of sufficient strength to last throughout the use in the treatment phase.

BACKGROUND OF THE INVENTION

Heretofore it has been well known to provide orthodontic brackets for use in the straight-wire technique of orthodontic treatment where the archwire is generally straight and free of any bends and activated to apply forces through the construction of brackets wherein the angulation of the archwire slot and its orientation to the tooth upon which it is mounted is chosen for purposes of applying a desired corrective force. Accordingly, it has been common to use the archwire slots as a reference line for mounting in parallel relation with the occlusal plane of the mouth which thereafter through the construction of the brackets places the tie wings at an oblique angle to the reference line. This necessitates positioning the archwire slots in the tie wings such that the occlusal or gingival tie wing ends or tips may be weakened with respect to their attachment to the base portion of the bracket and which thereafter may cause failure during wearing by a patient. This is particularly evident in the use of plastic brackets which have been primarily used for purposes of aesthetics even though it is well known that a plastic bracket cannot be made as strong as a metal bracket.

Thus, cutting the slots in the tie wings at an angle such as disclosed in U.S. Pat. No. 3,477,128, where the tie wings are of equal length, will affect the integrity of the bracket.

The strength problem have referred to has been addressed in prior art brackets, such as the one disclosed in U.S. Pat. No. 4,415,330, but in this bracket the length of the tie wings is still equal and the gingival ends of the tie wings define a reference line that, while being parallel to the archwire slots, is inclined to the long axis of the tie wings such that it creates visual alignment problems when mounting the bracket on a tooth.

SUMMARY OF THE INVENTION

The present invention overcomes the above problems in providing a bracket having tie wings of sound integrity, thereby giving the entire bracket a strength factor that is important to the life of the bracket and particularly useful for plastic brackets and which also provides reference points along the gingival tips of the tie wings that extend normal to the long axis of the tie wings and enhance the alignment analysis when mounting a bracket on a tooth. The bracket of the present invention provides tie wings of unequal length as well as tips or ends of the tie wings being of unequal length, while maintaining tie wing end strength and producing a trapezoidal tie wing configuration when viewed from the front elevational side. This is accomplished by centrally disposing the slots on the wings. Yet, the bracket of the invention retains the reference points which allow the tie wings to be aligned with the long axis of the tooth and the archwire slots to be aligned with the occlusal plane as well as the horizontal reference points along the gingival tie wing ends enhancing the alignment in a perpendicular relation to the long axis of the tooth and in parallel relation to the occlusal surface of the tooth.

It is therefore an object of the present invention to provide a new and improved orthodontic bracket for use in the straight-wire technique which enhances the mounting of the bracket on a tooth and also provides a bracket of greater strength to permit the use of the bracket in plastic and enhance its life.

Other objects, features and advantages of the invention will be apparent from the following detailed disclosure, taken in conjunction with the accompanying sheet of drawings, wherein like reference numerals refer to like parts.

BRIEF DESCRIPTION OF THE DRAWINGS

FIG. 1 is a front elevational view of the bracket of the present invention and showing the manner in which welding flanges may be added at each end where the flanges are shown in phantom;

FIG. 2 is an end elevational view of the bracket of FIG. 1 taken substantially along line 2—2 of FIG. 1;

FIG. 3 is a front elevational view of the bracket according to the invention representing how it may be mounted on a base that is thereafter mounted on a tooth and the manner in which it is aligned to the tooth;

FIG. 4 is a view of the bracket in FIG. 3 and removed from a tooth;

FIG. 5 is a sectional view of the bracket of FIG. 4 taken generally along line 5—5 of FIG. 4;

FIG. 6 is a front elevational view of a prior art bracket mounted on a tooth; and FIG. 7 is a side elevational view of the bracket shown in FIG. 6 to illustrate the weak point effected by cutting the archwire slots at an angle.

DESCRIPTION OF THE PREFERRED EMBODIMENTS

The bracket of the present invention, when made of metal, would be attachable to a bonding base or a band by soldering or welding and, when made of plastic, would be directly attachable to a tooth by bonding. When the bracket is mounted on a band, the band is in turn cemented on a tooth. When it is of metal and mounted on a bonding base, the base is then bonded to a tooth. Bonding is accomplished by any suitable bonding techniques. Further, when the bracket is made of metal for soldering to a band or bonding base, it need not include welding flanges; when it is made to be welded to a band or bonding base, welding flanges are provided at each end. The bracket, when made of metal, may be either cast from a suitable metal such as stainless steel or machined from suitable stock. When the bracket is made of plastic, it is suitably molded from a suitable plastic that may either be clear, tooth colored, or otherwise colored.

Referring now to the bracket of the invention, as shown in FIG. 1, it is illustrated in solid lines in a form that would be made for soldering the bracket when of metal to a welding flange or bonding base, while the addition of welding flanges is illustrated in phantom where it could be suitably welded to a band or bonding base. This bracket includes a base portion 10 and a pair of spaced tie wings 11 and 12 extending outwardly from the base portion. The bracket may be oriented such that either tie wing is mesial or distal, but for purposes of describing the invention herein tie wing 11 will be considered the mesial tie wing and tie wing 12 will be considered the distal tie wing. Mesial tie wing 11 includes a gingival end or tip 14 and an occlusal end or tip 15, while distal tie wing 12 includes a gingival tip or end 16 and an occlusal tip or end 17. A buccolabial opening archwire slot 20 is defined between the gingival and occlusal tie wing tips 14 and 15, while a buccolabial opening archwire slot 21 is defined between the gingival and occlusal tie wing tips 16 and 17. The slots are mutually aligned with one another, collectively defining the archwise slot of the bracket, for receiving an archwire of either round or rectangular cross section, although it is generally considered that this bracket is used for the edgewise technique and therefore would receive a rectangular archwire. Further, the aligned slots 20 and 21 define a reference line 22 which extends therethrough for the purpose of assisting in the description of the invention and the orientation of the bracket on a tooth.

The mesial tie wing 11 includes parallel opposed mesial and distal sides 24 and 25 and upper and lower or gingival and occlusal faces 26 and 27. Likewise, the distal tie wing 12 includes parallel opposed mesial and distal sides 30 and 31, and top and bottom or gingival and occlusal faces 32 and 33.

The tie wings are parallel to each other and extend obliquely to the reference line 22. The upper faces 26 and 32 of the tie wings are axially aligned and extend at an angle to the reference line 22. When mounting the bracket on a tooth, the bracket is preferably centered along the long axis of the tooth as indicated by the line 35 in FIG. 3 and where the tie wings extend generally parallel to that long axis. Further, the horizontal plane including the upper tie wing faces 26 and 32 extends substantially perpendicular to the long axis 35, while the reference line extending through the archwire slot extends obliquely to the long axis.

A further point of reference is the upper edge 37 of the base portion 10 as it extends parallel to the plane going through the upper tie wing surfaces 26 and 32 and perpendicular to the tie wings. The lower edge 38 extends at an angle to the upper edge and the width of the base is such that it substantially disposes the archwire slot through the major center portion of the base. When mounting the bracket on a tooth, the upper edge 37 together with the end faces 26 and 32 assist in properly orienting the bracket on a tooth. To the closest extent possible the archwire slot is cut or formed through the tie wings centrally of the tie wings.

The addition of welding flanges at each end of the bracket may be provided for the bracket if it is to be welded to a band or bonding base and then these flanges would take the general form illustrated in phantom and identified by numerals 40 and 41.

When the bracket is to be molded of plastic, it will then have molded integrally with the base portion 10 a bonding base 46 as shown in FIG. 4. The vertical and horizontal axes of the bonding base are essentially disposed centrally of the bracket, and the bracket is arranged relative to the bonding base such that the horizontal upper edge 37 of the base portion 10 parallels the horizontal axis through the base, while the vertical axes of the tie wings parallel the vertical axis of the base.

Similarly, when the bracket of FIG. 1 is soldered or welded to a bonding base, it is oriented relative to the bonding base as indicated in FIGS. 3 and 4.

The manner in which the archwire slot is shown in the bracket of FIGS. 1 and 2, where it is from the frontal view angularly related to the horizontal axis of the bracket, will be used for a tipping action on the tooth, and where the slot is angularly inclined to the bracket as from front to back, as shown in FIG. 2, will function to provide a torquing action to a tooth. No tipping action is provided when the archwire slot, as seen from the front, extends parallel to the horizontal axis of the bracket, and not torquing action is obtained when the slot, as seen from the side view, extends horizontally with respect to the bracket.

The bracket illustration of FIG. 3, when viewed from the front, may be considered either as a metal bracket mounted on a bonding base or a plastic bracket having an integrally formed bonding base. In either case, it will look the same.

When mounting the bracket and base assembly on a tooth 43, the reference line 22 is disposed in parallel orientation to the occlusal plane of the patient's mouth as represented by line 47, while the horizontal axis of the bracket and base assembly is disposed parallel to the occlusal plane of the tooth represented by the line 48. Further, inasmuch as the upper horizontal edge 37 of the base portion 10 is parallel to the horizontal axis of the bracket and base assembly, it provides a reference line for disposing the bracket perpendicular to the long axis 35 of the tooth, and still further, since the upper gingival faces 26 and 32 of the tie wings 11 and 12 fall in the same horizontal plane as represented by the line 50, that assists in the proper placement of the bracket on the tooth, as this line also would extend perpendicular to the long axis 35 of the tooth. It may also be noted that the gingival and occlusal faces of the tie wings, together with the mesial side of tie wing 11 and the distal side of tie wing 12, form a trapezoidal configuration whereby the archwire slot extends substantially centrally through the opposite ends of each of the tie wings. This is important from the standpoint of particularly making the bracket in plastic and obtaining the strongest possible tie wing tip configurations relative to the base for enhancing the life of the plastic bracket and inhibiting failures as was common in the prior art bracket illustrated in FIGS. 6 and 7. Noting particularly FIG. 7, a weak point exists at the lower end of the bracket at the narrow portion in the circled dotted line 55 which often caused failure during treatment. As seen particularly in FIGS. 2 and 5, the bracket of the present invention avoids such weak areas, particularly because one tie wing is made longer than the other, as shown in FIGS. 1, 3 and 4. Thus, the tie wings of the bracket of the present invention are of unequal length, and while the tie wing tips may not be of the exact same length, they are essentially the same whereby the archwire slot is generally centrally located through both tie wings. Thus, the trapezoidal configuration of the tie wings significantly enhances alignment of the bracket on the tooth and also contributes to the added strength by allowing the archwire slots of the tie wings to be generally centrally disposed and thereby avoiding areas of weakness.

It will be understood that modifications and variations may be effected without departing from the scope of the novel concepts of the present invention, but it is understood that this application is to be limited only by the scope of the appended claims.

The invention is hereby claimed as follows:

1. An orthodontic bracket for use with an archwire to impart corrective forces to a tooth comprising,
   a base portion for attachment to the tooth,
   a mesial tie wing integral with an extending from the base portion, said mesial tie wing having a gingival tip and an occlusal tip and a buccolabial opening archwire slot between the tips,
   a distal tie wing integral with and extending from the base portion and in parallel spaced relation to said mesial tie wing, said distal tie wing having a gingival tip and an occlusal tip and a buccolabial opening archwire slot between the tips and aligned with the slot in said mesial tie wing,
   each of said tie wings having parallel mesial and distal sides,
   said archwire slots defining a reference line for orientation parallel to the occlusal plane of a patient,
   the tie wings being oriented such that said sides are obliquely angled to said reference line, whereby said tie wings can be generally vertically disposed parallel to the tooth long axis and still be inclined at an oblique angle to said reference line,
   said gingival tips of said tie wings have top surfaces angularly disposed to said reference line and perpendicular to the vertical axis of the bracket and the mesial and distal sides of the wings and said occlusal tips having bottom surfaces parallel to said reference line,
   whereby the outer borders of said tie wings for a trapezoidal configuration and the axis of said archwire slots is disposed relative to said tie wings so that said gingival tips and said mesial tips of said tie wings are of unequal size and the top surface of the gingival tie wings facilitate the mounting of the bracket such that the top surfaces may be disposed to extend substantially perpendicular to the long axis of a tooth.

2. The orthodontic bracket of claim 1, which further includes welding flanges extending from said base portion.

3. The orthodontic bracket of claims 1 or 2, which is molded of plastic.

4. The orthodontic bracket of claim 1, wherein said archwire slots are centrally disposed on said tie wings.

5. The orthodontic bracket of claim 1, which is made of metal.

6. An orthodontic bracket assembly for use with an archwire to impart corrective forces on a tooth, including:
   a base pad for attachment to the tooth,
   a bracket mounted on said base pad comprising,
   a base portion secured to said base pad,
   a distal tie wing extending from said base portion and including a gingival tip and an occlusal tip defining between them an archwire slot,
   a mesial tie wing extending from said base portion and including a gingival tip and an occlusal tip defining between them an archwire slot, each of said distal and mesial tip wings having parallel distal and mesial sides,
   said archwire slots being in mutual alignment and providing a reference line for orientation parallel to the occlusal plane of a patient,
   said sides of said tie wings being inclined at an oblique angle to said reference line, whereby and tie wings can be generally vertically disposed parallel to the tooth along axis and still be inclined at an oblique angle to said reference line,
   said gingival tips of said tie wings having top surfaces angularly disposed to said reference line and perpendicular to the vertical axis of the bracket and the mesial and distal sides of the wings and said occlusal tips having bottom surfaces parallel to said reference line,
   whereby said tie wings together form a trapezoidal configuration and the axis of said archwire slots is disposed to said tie wings so that said gingival tips and said occlusal tips of the distal and mesial tie wings are of unequal size and the top surface of the gingival tie wings facilitate the mounting of the bracket such that the top surfaces may be disposed to extend substantially perpendicular to the long axis of a tooth.

7. The orthodontic bracket of claim 6, wherein said archwire slots are disposed centrally of said tie wings.

8. The orthodontic bracket of claim 6, wherein said base portion includes a top edge paralleling the top surfaces of said gingival tie wings and which align perpendicular to the long axis of the tooth and parallel to the horizontal axis of said base pad.

* * * * *

UNITED STATES PATENT AND TRADEMARK OFFICE
CERTIFICATE OF CORRECTION

PATENT NO. : 4,536,154
DATED : August 20, 1985
INVENTOR(S) : Robert E. Garton, Jr. and John E. Viglietti It is certified that error appears in the above-identified patent and that said Letters Patent are hereby corrected as shown below:

```
Col. 1, line 43, change "have" to --above--;
Col. 4, line 13, change "not" to --no--;
Col. 5, line 7,  change "an" to --and--;
        line 26, change "have" to --having--;
        line 32, change "for" to --form--;
Col. 6, line 21, change "and" to --said--; and
        line 23, change "along" to --long--.
```

Signed and Sealed this

Tenth Day of November, 1987

Attest:

DONALD J. QUIGG

Attesting Officer

Commissioner of Patents and Trademarks